United States Patent
Hosono et al.

(10) Patent No.: US 7,572,224 B2
(45) Date of Patent: Aug. 11, 2009

(54) ULTRASONIC PROBE AND ULTRASONIC DIAGNOSTIC APPARATUS

(75) Inventors: Yasuharu Hosono, Yokohama (JP); Yohachi Yamashita, Yokohama (JP); Kazuhiro Itsumi, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 306 days.

(21) Appl. No.: 11/223,969

(22) Filed: Sep. 13, 2005

(65) Prior Publication Data
US 2006/0079785 A1 Apr. 13, 2006

(30) Foreign Application Priority Data
Sep. 30, 2004 (JP) .............................. 2004-286583

(51) Int. Cl.
*A61B 7/04* (2006.01)
(52) U.S. Cl. ................. 600/459; 600/462; 310/333; 310/311
(58) Field of Classification Search ............... 600/459; 310/334
See application file for complete search history.

(56) References Cited

U.S. PATENT DOCUMENTS

| | | | | |
|---|---|---|---|---|
| 4,756,808 A | * | 7/1988 | Utsumi et al. | 204/486 |
| 4,800,316 A | * | 1/1989 | Ju-Zhen | 310/327 |
| 5,187,402 A | * | 2/1993 | Fujita et al. | 310/322 |
| 6,278,224 B1 | * | 8/2001 | Sawada et al. | 310/334 |
| 2002/0161301 A1 | | 10/2002 | Venkataramani et al. | |
| 2003/0032884 A1 | * | 2/2003 | Smith et al. | 600/459 |
| 2003/0083573 A1 | | 5/2003 | Azuma et al. | |
| 2004/0113522 A1 | * | 6/2004 | Nagahara et al. | 310/326 |
| 2004/0124746 A1 | * | 7/2004 | Suzuki et al. | |
| 2006/0079785 A1 | | 4/2006 | Hosono et al. | |

FOREIGN PATENT DOCUMENTS

| | | | |
|---|---|---|---|
| JP | 5-15530 | | 1/1993 |
| JP | 2004104629 | * | 2/2004 |
| JP | 2004-104629 | | 4/2004 |
| JP | 2004-120283 | | 4/2004 |

OTHER PUBLICATIONS

U.S. Appl. No. 11/150,276, filed Jun. 13, 2005, Yamashita, et al.
U.S. Appl. No. 11/223,969, filed Sep. 13, 2005, Hosono, et al.
U.S. Appl. No. 11/477,470, filed Jun. 30, 2006, Yamashita, et al.
U.S. Appl. No. 11/533,150, filed Sep. 19, 2006, Yamashita, et al.

* cited by examiner

*Primary Examiner*—Quyen Leung
*Assistant Examiner*—Bryan P Gordon
(74) *Attorney, Agent, or Firm*—Oblon, Spivak, McClelland, Maier & Neustadt, P.C.

(57) ABSTRACT

The present invention relates to an ultrasonic probe including a piezoelectric element, a first acoustic matching layer provided on the front face of the piezoelectric element and formed of a solid inorganic material, and a second acoustic matching layer provided on the first acoustic matching layer and formed of a mixture of an organic resin and 10 to 30% by volume of oxide powder with a density of 6.5 g/cm$^3$ or more.

20 Claims, 2 Drawing Sheets

ULTRASONIC PROBE AND ULTRASONIC DIAGNOSTIC APPARATUS

CROSS-REFERENCE TO RELATED APPLICATIONS

This application is based upon and claims the benefit of priority from prior Japanese Patent Application No. 2004-286583, filed Sep. 30, 2004, the entire contents of which are incorporated herein by reference.

BACKGROUND OF THE INVENTION

1. Field of the Invention

The present invention relates to an ultrasonic probe and an ultrasonic diagnostic apparatus.

2. Description of the Related Art

In the field of a medical ultrasonic diagnostic apparatus and a nondestructive inspection instrument, an ultrasonic probe is used for imaging the inner state of an object. The ultrasonic probe transmits ultrasonic waves toward the object and receives reflected echoes from an interface at which acoustic impedance changes in the object. In particular, the ultrasonic probe used in the medical ultrasonic diagnostic apparatus is formed in an array in which many oblong-shaped piezoelectric transducers are arranged, making it possible to acquire a real-time tomogram image with high resolution by electronically controlling the ultrasonic beam.

A typical ultrasonic probe comprises a piezoelectric element including a piezoelectric material and electrodes formed on both surfaces thereof, a backing material formed on the back face of the piezoelectric element, and an acoustic matching layer formed on the front face of the piezoelectric element, and has a structure that the piezoelectric element and the acoustic matching layer are processed into an array. In general, an acoustic lens is formed on the acoustic matching layer. The electrodes formed on both surfaces of the piezoelectric material are connected to a flexible printed circuit board (FPC) and are connected further to a diagnostic apparatus.

The piezoelectric element is used as a transmitter receiver for the ultrasonic waves. The backing material is used for absorbing undesired ultrasonic waves radiated backward from the piezoelectric element. The acoustic matching layer is used for improving the efficiency of transmitting/receiving the ultrasonic waves by matching the acoustic impedances between the piezoelectric element and the human body. Therefore, the acoustic impedance of the acoustic matching layer is set to a range between that of the piezoelectric element (20 to 30 Mrayls) and that of the human body (1.5 Mrayls). In the case of using two or more acoustic matching layers, the acoustic impedances of the acoustic matching layers are set to be gradually diminished toward the human body. The reason why the acoustic matching layer is processed into an array together with the piezoelectric element is to suppress coupling between adjacent channels. The pitch of the array probe is set to approximately 0.1 to 0.2 mm in a smaller case. The acoustic lens plays a role of focusing the ultrasonic waves in transmitting/receiving.

An ultrasonic probe used for diagnosis of the heart or the liver in a human boy is required to have a resonance frequency of approximately 2 to 5 MHz. An ultrasonic probe used for diagnosis of, for example, the carotid artery positioned shallower than the heart and the liver is required to have a higher resonance frequency. In order to provide a higher resonance frequency, it is necessary to reduce the thickness of the piezoelectric material, which is in the vibrating direction. Further, in order to suppress undesired vibrations, it is necessary to set the width of the piezoelectric material in the array direction at 60% or less of the thickness.

Conventionally, lead zirconate titanate (PZT) piezoelectric ceramics has been used for the piezoelectric material, since it has a high electromechanical coupling coefficient $k_{33}'$ of approximately 70% and permits a high conversion efficiency from electric signals to mechanical vibrations. Also, a piezoelectric material with a very high electromechanical coupling coefficient $k_{33}'$ of approximately 80 such as $Pb((Zn_{1/3}Nb_{2/3}))_{0.91}Ti_{0.09})O_3$ piezoelectric single crystal made of a solid solution of lead zinc niobate and lead titanate has been developed in recent years, and application of the particular piezoelectric material to the ultrasonic probe is being studied.

The acoustic matching layer is formed on the front face of the piezoelectric element to improve transmitting/receiving efficiency of ultrasonic waves to the human body. An acoustic matching layer made of a material prepared by dispersing metal particles such as W particles in an organic resin has been known. In recent years, an acoustic matching layer made of a material prepared by dispersing zinc oxide particles in an organic resin has also been proposed (see Japanese Patent Disclosure No. 2004-104629).

However, if an ultrasonic probe is manufactured by using the above acoustic matching layer, such problems as follows would occur.

When the acoustic matching layer prepared by dispersing metal particles in an organic resin is used, it is necessary to cut the high-toughness metal hard to be cut. This brings about marked degradation of a cutting blade in array processing by dicing. Where the processing is continued using the degraded blade, chipping or crack is created in the piezoelectric material that is cut together with the acoustic matching layer. The chipping or crack created in the piezoelectric material gives rise to a nonuniform capacity of the piezoelectric element, which leads directly to the nonuniform sensitivity of the ultrasonic probe so as to lower the quality of a converted image.

On the other hand, in the case of the acoustic matching layer prepared by dispersing zinc oxide particles in an organic resin, it is necessary to increase the amount of the dispersed resin in order to provide desired acoustic impedance because the density of zinc oxide is low. Increase in the amount of the zinc oxide decreases the amount of the resin between the adjacent oxide particles so as to lower adhesion of the particles. Accordingly, the array processing by dicing causes significant shedding, resulting in a problem that highly-accurate fine processing cannot be achieved. Also, the acoustic matching layer may be used with covered by plated metal over the entire surface thereof. In this case, adhesion between the acoustic matching layer and the plated metal is so insufficient that the electrode may be stripped away during array processing by dicing. Since the electrode of the piezoelectric element on the side of the acoustic matching layer is connected to the ground plate via the electrode formed on the acoustic matching layer, loss of the electrode causes open-circuit defect. Further, it is possible that the open-circuit defect may be caused during use of the ultrasonic probe.

BRIEF SUMMARY OF THE INVENTION

An ultrasonic probe according to an aspect of the present invention, comprises: a piezoelectric element; a first acoustic matching layer provided on the front face of the piezoelectric element and formed of a solid inorganic material; and a second acoustic matching layer provided on the first acoustic matching layer and formed of a mixture of an organic resin and 10 to 30% by volume of oxide powder with a density of 6.5 g/cm$^3$ or more.

An ultrasonic diagnostic apparatus according to another aspect of the present invention, comprises: an ultrasonic probe comprising: an acoustic backing layer; a piezoelectric element provided on the front face of the acoustic backing layer; a first acoustic matching layer provided on the front face of the piezoelectric element and formed of a solid inorganic material; a second acoustic matching layer provided on the front face of the first acoustic matching layer and formed of a mixture of an organic resin and 10 to 30% by volume of oxide powder with a density of 6.5 g/cm$^3$ or more; and an acoustic lens provided on the front face of the second acoustic matching layer, and a ultrasonic-probe control unit connected to the ultrasonic probe via a cable.

DETAILED DESCRIPTION OF THE INVENTION

An ultrasonic probe according to an embodiment of the present invention will be described with reference to drawings.

Figure 1:
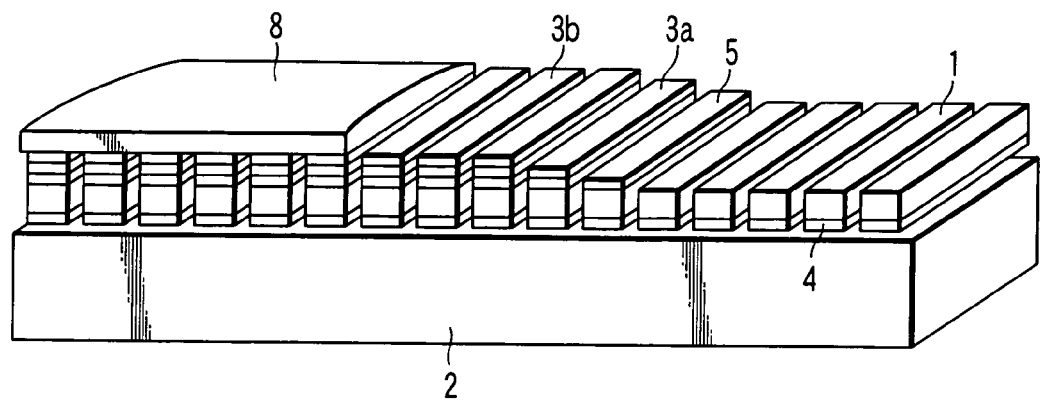
FIG. 1 is a perspective view showing an ultrasonic probe according to an embodiment of the present invention.

FIG. 1 is a partly-exploded perspective view showing an ultrasonic probe according to an embodiment of the present invention. As shown in FIG. 1, the ultrasonic probe according to the embodiment of the present invention comprises an acoustic backing material 2, a piezoelectric material 1 formed on the backing material 2, a second electrode 4 formed on the back face of the piezoelectric material 1 facing the acoustic backing material 2, a first electrode 5 formed on the front face of the piezoelectric material 1, a first acoustic matching layer 3a formed on the first electrode 5, and a second acoustic matching layer 3b formed on the first acoustic matching layer 3a. In the ultrasonic probe according to the embodiment of the present invention, the first acoustic matching layer 3a is formed of a solid inorganic material, and the second acoustic matching layer 3b is formed of a material prepared by dispersing 10 to 30% by volume of an oxide powder with a density of 6.5 g/cm$^3$ or more in an organic resin. The acoustic impedance of the second acoustic matching layer 3b is smaller than that of the first acoustic matching layer 3a. The stack of the piezoelectric element including the piezoelectric material 1 sandwiched between the first electrode 5 and the second electrode 4, the first acoustic matching layer 3a and the second acoustic matching layer 3b is divided into channels so as to form array. An acoustic lens 8 is formed on the second acoustic matching layer 3b in FIG. 1. However, the ultrasonic probe of the present invention is not limited to the construction shown in FIG. 1. For example, it is possible that the acoustic matching layer may comprise three- or four-layered structure. If the impedance values of the acoustic matching layers are set to a range between that of the piezoelectric material (20 to 30 Mrayls) and that of the human body (1.5 Mrayls) and so as to gradually approach the value for the human body, transmitting/receiving efficiency of ultrasonic waves can be further improved. Also, where the stack of the piezoelectric element, the first acoustic matching layer 3a and the second acoustic matching layer 3b is two-dimensionally arrayed, resolution and the sensitivity can be markedly improved even when the acoustic lens 8 is not formed on the second acoustic matching layer 3b.

In the ultrasonic probe according to an embodiment of the present invention, the first acoustic matching layer 3a in contact with the piezoelectric element is formed of a solid inorganic material, and the second acoustic matching layer 3b is formed of a material prepared by dispersing 10 to 30% by volume of an oxide powder with a density of 6.5 g/cm$^3$ or more in an organic resin. The use of a plurality of acoustic matching layers improves acoustic impedance matching so as to improve transmitting/receiving efficiency of ultrasonic waves. Also, use of the above materials for the first and second acoustic matching layers 3a, 3b suppresses chipping and crack of the piezoelectric material in array processing by dicing, making it possible to reduce dispersion of the capacity, and further to reduce dispersion of sensitivity of the ultrasonic probe.

In an embodiment of the present invention, the solid inorganic material used for the first acoustic matching layer acts as a support plate of the piezoelectric material in array processing and plays a role of suppressing misalignment of the blade. The solid inorganic material used for the first acoustic matching layer includes a ceramics including $SiO_2$, $MgO$ and $Al_2O_3$, a ceramics including $Si_3N_4$, $AlN$, $Al_2O_3$ and $ZrO_2$, a ceramics including calcium silicate and lithium aluminosilicate, a fluorophlogopite ceramics, and a hexagonal boron nitride ceramics. One or a plurality of ceramics selected from the above group can be used in the present invention. It is also possible to add an additive element to the above solid inorganic material. In particular, the ceramics containing $SiO_2$, $MgO$ and $Al_2O_3$ exhibits a satisfactory processablity, bringing about decreased damage to the single crystal in dicing, and has a high mechanical strength, making it possible to improve the mechanical strength of the ultrasonic probe.

The reason that the density and the amount of the oxide powder used in the second acoustic matching layer are limited in an embodiment of the present invention will be described. In the case of loading an oxide powder with a density lower than 6.5 g/cm$^3$, it is necessary to increase the amount of the oxide powder in order to realize acoustic impedance desirable for the second acoustic matching layer. Increase in the amount of the oxide powder dispersed in the resin decreases the amount of the resin between the neighboring oxide powders, which lowers adhesion of the particles with the result that shedding of the oxide powder is caused in polishing or dicing. If the shedding is caused, it is difficult to obtain desired dimensional accuracy and gives rise to a problem that mechanical strength is markedly lowered in fine processing. Even if the density of the oxide powder is 6.5 g/cm$^3$ or more, the oxide powder exceeding 30% by volume is undesirable because a similar problem as above is caused. Where the amount of the oxide powder is smaller than 10% by volume or exceeds 30% by volume, the acoustic impedance is deviated from the range desirable for the second acoustic matching layer so as to give rise to a problem that the transmitting/receiving efficiency of the ultrasonic waves is lowered.

In the ultrasonic probe according to an embodiment of the present invention, it is desirable that the second acoustic matching layer is formed of a material made of an organic resin containing 10 to 30% by volume of oxide powder of a perovskite structure containing 50% or more of PbO and 1% or more of $Nb_2O_5$. When the oxide powder of the perovskite structure containing at least 50% of PbO and at least 1% of $Nb_2O_5$ is dispersed in the organic resin, the oxide powder can be dispersed uniformly in the organic resin so as to suppress shedding in array processing by dicing. Further, the oxide powder of the perovskite structure contains the composition used as a raw material of the piezoelectric material, making it possible to improve adhesion between the second acoustic matching layer and the plated metal when the second acoustic matching layer is plated with a metal. As a result, it is possible to suppress stripping of the electrode in the array processing.

In the ultrasonic probe according to an embodiment of the present invention, a material for the second acoustic matching layer is preferably made of an organic resin containing 10 to 30% by volume of at least one metal oxide selected from the group consisting of $CeO_2$, $Pr_2O_3$, $Nd_2O_3$, $Yb_2O_3$, and $Lu_2O_3$. When the above oxide powder is dispersed in the organic resin, the oxide powder can be dispersed uniformly in the organic resin so as to suppress shedding in array processing by dicing.

As described above, in the second acoustic matching layer included in the ultrasonic probe according to an embodiment of the present invention, shedding of the oxide powder dispersed in the resin can be markedly suppressed in array processing, making it possible to finish fine processing with high accuracy. Also, since the second acoustic matching layer exhibits very good adhesion to a plated metal (Au, Ni), it is possible to suppress stripping of the electrode in array processing, thereby suppressing defective conduction of the element.

In an embodiment of the present invention, as a piezoelectric material, a single crystalline material having a composition represented by, for example, $Pb(B1_{1-x}, Ti_x)O_3$, where $0.3 \leq x \leq 0.6$ and B1 is at least one element selected from the group consisting of Zr, Sn and Hf, may be used. Such a piezoelectric material of a solid-solution single crystal enables to lower a sound velocity therein compared with a piezoelectric material consisting of a piezoelectric ceramics, making it possible to provide a high-sensitivity ultrasonic probe. If x in the general formula noted above is smaller than 0.3, the Curie temperature of the piezoelectric single crystal is lowered, with the result that the piezoelectric single crystal tends to be depolarized during dicing. On the other hand, if x exceeds 0.6, it is difficult to provide a high electromechanical coupling coefficient. In addition, the dielectric constant is lowered so as to make it difficult to take matching of electric impedances in transmitting/receiving.

In an embodiment of the present invention, as a piezoelectric material, a single crystalline material having a composition represented by $Pb(B1, B2)_{1-x}Ti_xO_3$, where $0.04 \leq x \leq 0.55$, B1 is at least one element selected from the group consisting of Zn, Mg, Ni, Sc, In and Yb, and B2 is at least one element selected from the group consisting of Nb and Ta, may be used. Such a piezoelectric material of a solid-solution single crystal enables to realize a high coupling coefficient and a low sound velocity compared with a piezoelectric material consisting of a piezoelectric ceramics, making it possible to provide a high-sensitivity ultrasonic probe. If x in the general formula given above is smaller than 0.04, the Curie temperature of the piezoelectric single crystal is lowered, with the result that the piezoelectric single crystal tends to be depolarized during dicing. On the other hand, if x exceeds 0.55, it is difficult to provide a high electromechanical coupling coefficient. In addition, the dielectric constant is lowered so as to make it difficult to take matching of electric impedances in transmitting/receiving.

Since the single crystalline materials noted above exhibit piezoelectric characteristics superior to those of the conventional piezoelectric ceramics, improvement in performance of the ultrasonic probe can be expected when the single crystalline material is applied to an ultrasonic probe. It should be noted that, since the single crystalline material has low mechanical strength, crack and chipping may be occurred in dicing, which may be a cause of sensitivity dispersion. However, use of the acoustic matching layer containing the material described above enables to suppress the crack and chipping in the dicing, making it possible to manufacture a high-sensitivity, broadband single-crystalline probe that is low in sensitivity dispersion and high in reliability.

Figure 2:
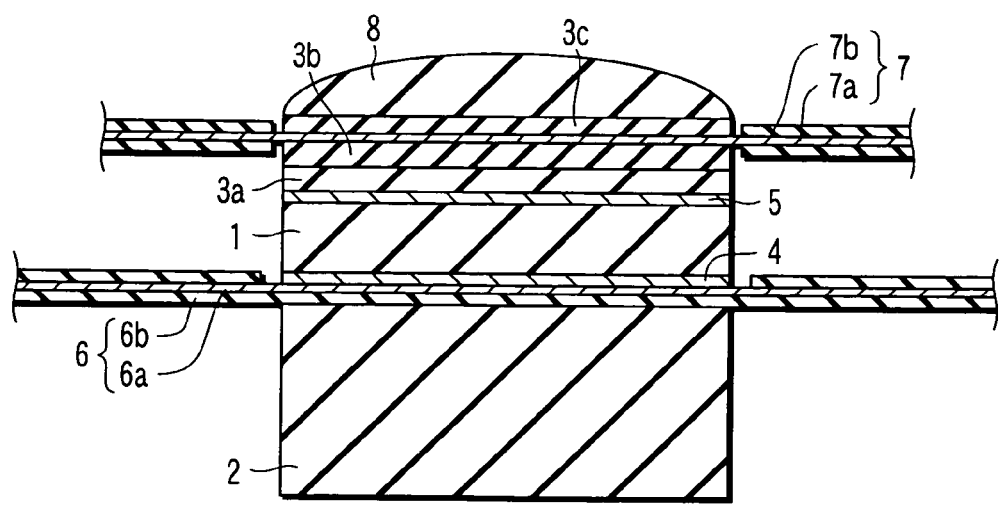
FIG. 2 is a cross-sectional view showing an ultrasonic probe according to an embodiment of the present invention.

The ultrasonic probe according to the embodiment of the present invention can be used as follows. As shown in FIG. 2, the first electrode 5 is connected to the ground plate 7 via a metal layer plated on the surface of the acoustic matching layer, and the second electrode 4 is connected to an ultrasonic diagnostic apparatus (not shown) via the flexible printed circuit board (FPC) 6. A driving signal voltage is applied from the ultrasonic diagnostic apparatus to the piezoelectric material 1 so as to vibrate the piezoelectric material 1 and, thus, to emit ultrasonic waves from the acoustic lens 8. In receiving the ultrasonic waves, the ultrasonic waves received on the acoustic lens 8 are converted into electric signals by the piezoelectric material 1. Further, after desired delays are applied to the received signals for respective channels by a beam former in the ultrasonic diagnostic apparatus, addition with phasing is performed in an adder in the ultrasonic diagnostic apparatus. Then, in the case of measuring the fundamental harmonic, the signals are passed through the fundamental-pass filter in the ultrasonic diagnostic apparatus and, in the case of measuring the second harmonic, the signals are passed through a high-pass filter in the ultrasonic diagnostic apparatus for removing the fundamental harmonic so as to form an on a monitor (not shown).

A method of manufacturing an ultrasonic probe according to an embodiment of the present invention will be described.

A method of manufacturing piezoelectric ceramics used as a piezoelectric material will be described. The following description covers the case of manufacturing lead zirconate-lead titanate solid-solution ceramics. As starting materials, high-grade PbO, $ZrO_2$ and $TiO_2$ powders are prepared. After purity correction is applied to these powders, they are weighed to have a desired molar ratio in terms of lead zirconate (PZ) and lead titanate (PT). Pure water is added to the weighed powders, followed by mixing for a prescribed time with a ball mill having, for example, $ZrO_2$ balls housed therein. After water is removed from the resultant mixture, the mixture is sufficiently pulverized with a pulverizer such as a stone mill. Five percent by weight of polyvinyl alcohol is added to the pulverized powder, followed by applying mixing, granulation and pressing in a mold so as to provide a molded body. The molded body is put in a magnesia sheath and calcined at 500° C., followed by sintering the calcined body so as to provide a sintered body. The sintered body is polished and processed for outer shape. A conductive film is deposited on the sintered body by sputtering, and then the first electrode 5 and the second electrode 4 are formed by selective etching on the transmitting-receiving surface for ultrasonic waves and the back surface, respectively, of the piezoelectric material 1, to provide a piezoelectric element.

In the case of using a piezoelectric single crystal as a piezoelectric material, the piezoelectric single crystal is manufactured as follows. The following description covers the case of manufacturing a lead zinc niobate-lead titanate solid-solution single crystal. As starting materials, high-grade PbO, ZnO, $Nb_2O_5$ and $TiO_2$ powders are prepared. After purity correction is applied to these powders, they are weighed to have a desired molar ratio in terms of lead zinc niobate (PZN) and lead titanate (PT), followed by adding PbO as flux. Pure water is added to the weighed powders, followed by mixing for a prescribed time with a ball mill having, for example, $ZrO_2$ balls housed therein. After water is removed from the resultant mixture, the mixture is sufficiently pulverized with a pulverizer such as a stone mill. Further, the pulverized material is put in a rubber mold container so as to apply rubber pressing to the pulverized material under a desired pressure. The solid taken out of the rubber mold is put in a container made of, for example, platinum having a desired capacity so as to melt the solid at a desired temperature. After cooling, the container housing the solid is sealed with a lid made of, for example, platinum, and the container is set in the center of an electric furnace. The solid is heated to a temperature higher than the melting point thereof, followed by gradually cooling the solid to the temperature around the melting temperature at a desired cooling rate, followed by further cooling the solid to room temperature. A nitric acid of a desired concentration is added to the container and is boiled. Then, a solid-solution single crystal used as a piezoelectric single crystal is taken out. In the description given above, a flux method is employed for the growth of the single crystal. Alternatively, it is also possible to use a single crystalline material manufactured by, for example, the Bridgeman method, the Kyropoulos method, a hydrothermal growth method, a top seeded solution growth (TSSG) method, and a solid-state single crystal growth (SSCG) method. Also, lead zinc niobate-lead titanate is exemplified in the description given above. However, it is also possible to manufacture a solid-solution piezoelectric single crystal containing a lead titanate by substituting ZnO and $Nb_2O_5$ used as the starting materials with other oxides containing other elements. The single crystal is polished and processed for outer shape. A conductive film is deposited on the single crystal by sputtering, and then the first electrode 5 and the second electrode 4 are formed by selective etching on the transmitting-receiving surface for ultrasonic waves and the back surface, respectively, of the piezoelectric material 1, to provide a piezoelectric element.

The method of manufacturing an ultrasonic probe according to an embodiment of the present invention will be described. The following description covers the case where a piezoelectric ceramics is used as a piezoelectric material.

The first acoustic matching layer 3a having a conductive layer (not shown) formed by plating on the entire surface is bonded to the first electrode 5 of the manufactured piezoelectric element by using, for example, an epoxy adhesive. The first acoustic matching layer 3a is made of a solid inorganic material. Similarly, the second acoustic matching layer 3b having a conductive layer (not shown) formed on the entire surface is bonded to the first acoustic matching layer 3a. The second acoustic matching layer 3a is made of a mixture of an organic resin and 10 to 30% by volume of oxide powder with a density of 6.5 g/cm³ or more. The acoustic impedance of the second acoustic matching layer 3b is set smaller than that of the first acoustic matching layer 3a so as to achieve acoustic impedance matching with the object. Then, the FPC 6 having conductive cables 6a formed on an insulating layer 6b is bonded to the second electrode 4 of the piezoelectric element by using, for example, an epoxy adhesive. Then, the resultant structure is bonded to the acoustic backing material 2 such that the FPC 6 is in contact with the acoustic backing material 2. Dicing of the resultant structure is performed with a blade several times from the acoustic matching layer to reach the FPC 6 by which channels each formed of a stack of the piezoelectric element and the acoustic matching layer are arrayed and separated with each other on the acoustic backing material 2. Then, the ground plate 7 comprising an insulating layer 7b and a conductive layer 7a formed thereon by plating is bonded to the second acoustic matching layer 3b by using, for example, an epoxy adhesive. Further, a third acoustic matching layer 3c is bonded to the ground plate 7 by using an organic adhesive, followed by forming the acoustic lens 8 on the third acoustic matching layer 3c so as to provide an ultrasonic probe.

An ultrasonic probe can be manufactured by the same method as above in the case of using a piezoelectric single crystal as the piezoelectric material. Where the piezoelectric single crystal used as the piezoelectric material 1 has a rhombohedral or a pseudo cubic crystal system, it is desirable for the ultrasonic wave transmitting/receiving surface of the single crystal on the side of the first electrode 5 to be formed of a (001) plane. Such a piezoelectric material 1 is prepared by cutting the piezoelectric crystal in a direction perpendicular to the [001] axis (C axis) thereof.

Each of the first electrode 5 and the second electrode 4 may be formed of a two-layered conductor such as Ti/Au, Ni/Au and Cr/Au, or baking silver containing glass frit. Although the acoustic matching layer is of a two-layered or three-layered structure In the embodiment described above, a multi-layered structure including four or more layers may be used. Although the ground plate 7 is adhered to the second acoustic matching layer 3b on which a conductive layer is sputtered, the ground plate 7 need not be adhered to the entire surface of the second acoustic matching layer 3b. The ground plate 7 may be adhered only to the both edge portions of the second acoustic matching layer 3b. Also, the ground plate 7 may be adhered to the first acoustic matching layer 3a.

EXAMPLES

The present invention will now be described in more detail with reference to Examples, but the present invention is not limited to the following Examples.

Example 1

As starting materials, high-grade PbO, $ZrO_2$ and $TiO_2$ powders are prepared. After purity correction is applied to these powders, they are weighed to have a molar ratio of 53:47 in terms of lead zirconate (PZ) and lead titanate (PT). Pure water is added to the weighed powders, followed by mixing for a prescribed time with a ball mill having, for example, $ZrO_2$ balls housed therein. After water is removed from the resultant mixture, the mixture is sufficiently pulverized with a pulverizer such as a stone mill. Five percent by weight of polyvinyl alcohol is added to the pulverized powder, followed by applying mixing, granulation and pressing in a mold so as to provide a molded body. The molded body is put in a magnesia sheath and calcined at 500° C., followed by sintering the calcined body at 1250° C. so as to provide a sintered body.

The sintered body is polished and processed into a piezoelectric material sized at 30 mm×20 mm×0.4 mm. A first and second electrodes made of Cr/Au are formed by sputtering to provide a piezoelectric element. Poling is performed for the piezoelectric element by applying an electric field of 3 kV/mm. The acoustic impedance of the piezoelectric element is found to be 30 Mrayls.

A first acoustic matching layer made of a ceramics containing $SiO_2$, MgO and $Al_2O_3$, exhibiting an acoustic impedance of 13 Mrayls, and having a Cr/Au electrode formed on the entire surface thereof by sputtering is bonded to the first electrode of the piezoelectric element by using an epoxy adhesive. A second acoustic matching layer is prepared by dispersing 10% by volume of cerium oxide ($CeO_2$) powder (density: 7.65 g/cm$^3$) in an epoxy resin and shaping into a flat plate, and applying polishing and outer-shape processing to the flat plate, followed by depositing a Cr/Au electrode by sputtering on the entire surface of the flat plate. The second acoustic matching layer is bonded to the first acoustic matching layer by using an epoxy adhesive. The acoustic impedance of the second acoustic matching layer is found to be 5 Mrayls. Then, an FPC having a conductive layer of Cu and an acoustic backing material are bonded successively to the second electrode of the piezoelectric element.

Next, the stack of the piezoelectric element and the acoustic matching layer is diced into an array at a pitch of 200 μm with a dicing saw having a blade with a thickness of 50 μm. A ground plate made of Au is bonded to the entire surface of the second acoustic matching layer by using an epoxy adhesive. A third acoustic matching layer made of a polyethylene sheet and exhibiting an acoustic impedance of 2 Mrayls is bonded to the ground plate by using an epoxy adhesive. Further, an acoustic lens made of silicone rubber is bonded to the third acoustic matching layer by using a silicone adhesive so as to provide an ultrasonic probe.

The capacitance of the piezoelectric material included in the resultant ultrasonic probe is measured from one end of the FPC at a frequency of 1 kHz. The average capacitance of the piezoelectric materials of 100 channels arrayed in the ultrasonic probe is found to be 90 pF, and capacitance dispersion is found to be 10% or less, which is satisfactory. Then, a coaxial cable having an electrostatic capacitance of 110 pF/m and having a length of 2 m is connected to the FPC so as to connect the ultrasonic probe to a diagnostic apparatus for evaluating the characteristics of the ultrasonic probe. The ultrasonic probe is found to have a high sensitivity and a wide band. In addition, the ultrasonic probe exhibits very low sensitivity dispersion of 15% or less among the channels.

Example 2

A second acoustic matching layer is prepared by dispersing 20% by volume of a mixture of oxide powders (density: 7.90 g/cm$^3$) including 65% by weight of PbO, 20% by weight of $ZrO_2$, 10% by weight of $TiO_2$, 1% by weight of MgO, and 4% by weight of $Nb_2O_5$ in an epoxy resin and shaping into a flat plate, and applying polishing and outer-shape processing to the flat plate, followed by depositing a Cr/Au electrode by sputtering on the entire surface of the flat plate. The acoustic impedance of the second acoustic matching layer is found to be 5 Mrayls. An ultrasonic probe is manufactured as in Example 1, except that the above second acoustic matching layer is used.

The capacitance of the piezoelectric material included in the resultant ultrasonic probe is measured as in Example 1 from one end of the FPC at a frequency of 1 kHz. The average capacitance of the piezoelectric materials of 100 channels arrayed in the ultrasonic probe is found to be 90 pF, and capacitance dispersion is found to be 8% or less, which is satisfactory. Also, the characteristics of the ultrasonic probe are evaluated as in Example 1. The ultrasonic probe is found to have a high sensitivity and a wide band. In addition, the ultrasonic probe exhibits very low sensitivity dispersion of 10% or less among the channels.

Example 3

First, lead indium niobate $Pb(In_{1/2}Nb_{1/2})O_3$ (PIN), lead magnesium niobate $Pb(Mg_{1/3}Nb_{2/3})O_3$ (PMN), and lead titanate $PbTiO_3$ (PT) are weighed in a molar ratio of 16:51:33 to prepare a mixed powder. Then, $0.16Pb(In_{1/2}Nb_{1/2})O_3$-$0.51Pb(Mg_{1/3}Nb_{2/3})O_3$-$0.33PbTiO_3$ (PIMNT 16/51/33), PbO used as flux, and $B_2O_3$ are weighed in molar ratio of PIMNT 16/51/33:PbO:$B_2O_3$=50:40:10 to prepare a mixed powder. The mixed powder is put in a platinum container with a volume of 200 cc and heated to 1250° C. to melt the powder, followed by cooling to room temperature so as to growth a solid-solution piezoelectric single crystal. Then, the direction of the <001> axis of the piezoelectric single crystal is determined by using a Laue camera, followed by slicing the single crystal by using a cutter in the direction perpendicular to the <001> axis to prepare a wafer with a thickness of 600 μm. The sliced piezoelectric single crystal is polished to a thickness of 350 μm and shaped into a piezoelectric material sized at 30 mm×20 mm×0.4 mm. A first and second electrodes made of Cr/Au are deposited on the piezoelectric material by sputtering so as to manufacture a piezoelectric element. Poling is performed for the piezoelectric element by applying an electric field of 1 kV/mm. The acoustic impedance of the piezoelectric element is found to be 25 Mrayls.

Then, an ultrasonic probe is manufactured as in Example 2. The capacitance of the piezoelectric material included in the resultant ultrasonic probe is measured as in Example 1 from one end of the FPC at a frequency of 1 kHz. The average capacitance of the piezoelectric materials of 100 channels arrayed in the ultrasonic probe is found to be 80 pF, and capacitance dispersion is found to be 15% or less, which is satisfactory. Also, the characteristics of the ultrasonic probe are evaluated as in Example 1. The ultrasonic probe is found to have a high sensitivity and a wide band. In addition, the ultrasonic probe exhibits very low sensitivity dispersion of 10% or less among the channels.

Example 4

A solid-solution single crystal made of lead stannate $PbSnO_3$ (PSn) and lead titanate $PbTiO_3$ (PT) is prepared as in Example 3. Then, an ultrasonic probe is manufactured as in Example 2. The capacitance of the piezoelectric material included in the resultant ultrasonic probe is measured as in Example 1 from one end of the FPC at a frequency of 1 kHz. The average capacitance of the piezoelectric materials of 100 channels arrayed in the ultrasonic probe is found to be 85 pF, and capacitance dispersion is found to be 14% or less, which is satisfactory. Also, the characteristics of the ultrasonic probe are evaluated as in Example 1. The ultrasonic probe is found to have a high sensitivity and a wide band. In addition, the ultrasonic probe exhibits very low sensitivity dispersion of 10% or less among the channels.

Comparative Example 1

An ultrasonic probe is manufactured as in Example 1, except that the first and second acoustic matching layers are prepared as follows.

The first acoustic matching layer is prepared by dispersing 40% by weight of tungsten metal powder in an epoxy resin and shaping into a flat plate, applying polishing and outer-shape processing to the flat plate, followed by depositing a Cr/Au electrode by sputtering on the entire surface of the flat plate. The acoustic impedance of the first acoustic matching layer is found to be 13 Mrayls. The first acoustic matching layer is bonded to the first electrode of the piezoelectric element by using an epoxy adhesive. The second acoustic matching layer is prepared by dispersing 60% by volume of a mixture of zinc oxide (ZnO) powder (density: 5.60 g/cm$^3$) and silica ($SiO_2$) powder (density of 2.65 g/cm$^3$) in an epoxy resin and shaping into a flat plate, and applying polishing and outer-shape processing to the flat plate, followed by depositing a Cr/Au electrode by sputtering on the entire surface of the flat plate. The second acoustic matching layer is bonded to the first acoustic matching layer by using an epoxy adhesive. The acoustic impedance of the second acoustic matching layer is found to be 5 Mrayls.

The capacitance of the piezoelectric material included in the resultant ultrasonic probe is measured as in Example 1 from one end of the FPC at a frequency of 1 kHz. The average capacitance of the piezoelectric materials of 100 channels arrayed in the ultrasonic probe is found to be 90 pF, and capacitance dispersion is found to be 20% or less, which is significantly large. Also, the ultrasonic probe includes three channels defective in conductivity. It is interpreted that the metal powder dispersed in the first acoustic matching layer increases load to the blade during array processing by dicing, which degrades the blade gradually. If the piezoelectric material is diced using the degraded blade with lowered dicing property, chipping and crack are caused in the piezoelectric material, bringing about capacitance dispersion. Also, since the second acoustic matching layer contains the oxide powder in an amount of greater than 30% by volume, adhesion between neighboring powder particles is lowered, bringing about shedding during array processing by dicing. It is possible that the electrode is partly stripped away together with the shedding, which may cause open-circuit defect. The characteristics of the ultrasonic probe are evaluated as in Example 1, with the result that sensitivity dispersion among the channels is very large, i.e., 25% or more, though the ultrasonic probe includes some channels having a high sensitivity and a wide band. The high sensitivity dispersion among the channels is found to give detrimental effect to the quality of the image displayed on the diagnostic apparatus.

Comparative Example 2

An ultrasonic probe is manufactured as in Example 1, except that the second acoustic matching layer is prepared as follows.

The first acoustic matching layer made of a ceramics containing $SiO_2$, MgO and $Al_2O_3$, exhibiting an acoustic impedance of 13 Mrayls, and having a Cr/Au electrode formed on the entire surface thereof by sputtering is bonded to the first electrode of the piezoelectric element by using an epoxy adhesive. The second acoustic matching layer is prepared by dispersing 60% by volume of a mixture of zinc oxide (ZnO) powder and silica ($SiO_2$) powder in an epoxy resin and shaping into a flat plate, and applying polishing and outer-shape processing to the flat plate, followed by depositing a Cr/Au electrode by sputtering on the entire surface of the flat plate. The second acoustic matching layer is bonded to the first acoustic matching layer by using an epoxy adhesive. The acoustic impedance of the second acoustic matching layer is found to be 5 Mrayls.

The capacitance of the piezoelectric material included in the resultant ultrasonic probe is measured as in Example 1 from one end of the FPC at a frequency of 1 kHz. The average capacitance of the piezoelectric materials of 100 channels arrayed in the ultrasonic probe is found to be 90 pF, and capacitance dispersion is found to be 15% or less, which is significantly large. Also, the ultrasonic probe includes one channel defective in conductivity. It is interpreted that the second acoustic matching layer contains the oxide powder in an amount of greater than 30% by volume, adhesion between neighboring powder particles is lowered, bringing about shedding during array processing by dicing. It is possible that the electrode is partly stripped away together with the shedding, which may cause open-circuit defect. The characteristics of the ultrasonic probe are evaluated as in Example 1, with the result that sensitivity dispersion among the channels is very large, i.e., 20% or more, though the ultrasonic probe includes some channels having a high sensitivity and a wide band. The high sensitivity dispersion among the channels is found to give detrimental effect to the quality of the image displayed on the diagnostic apparatus.

Example 5

Figure 3:
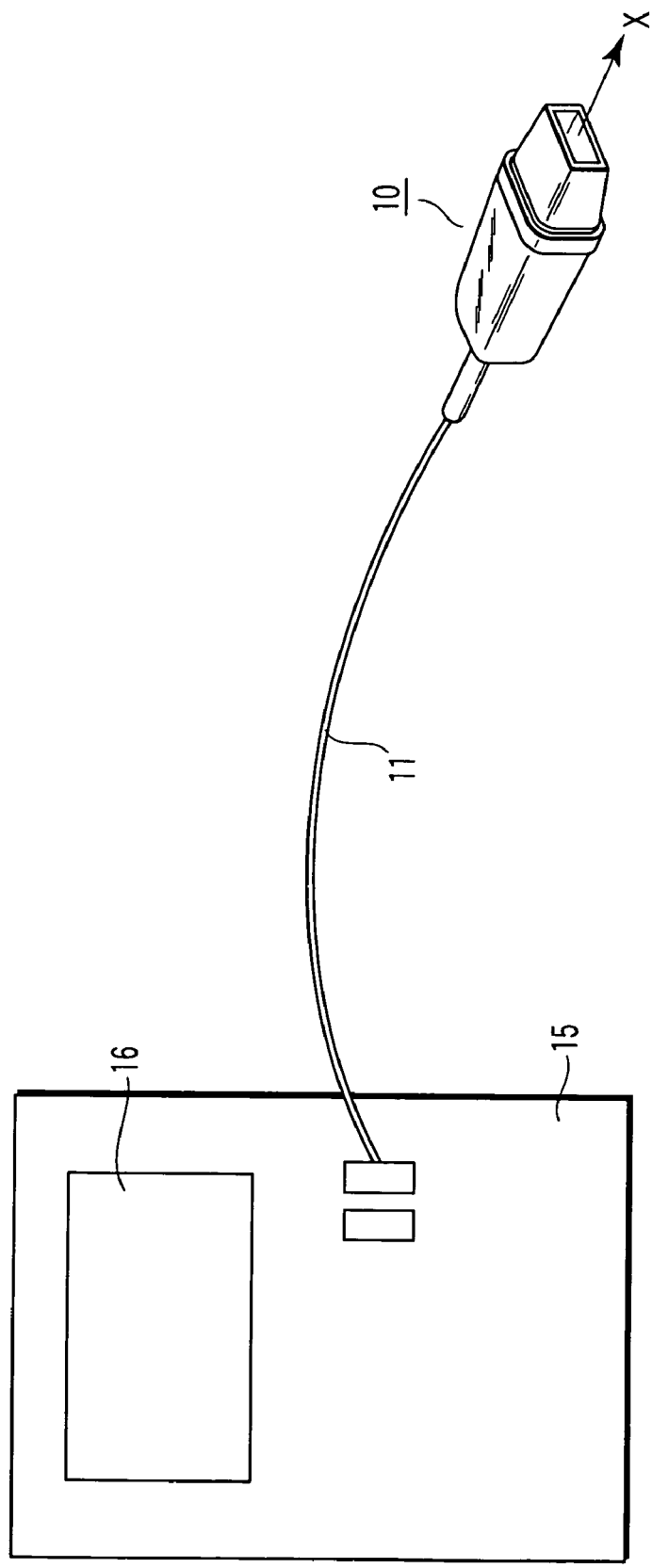
FIG. 3 is a schematic view showing an ultrasonic diagnostic apparatus in Example 5 of the present invention.

The ultrasonic diagnostic apparatus using the ultrasonic probe in Example 1 described above will be described with reference to FIG. 3. In a medical ultrasonic diagnostic apparatus or an ultrasonic image inspecting apparatus which transmits ultrasonic signals to an object and receives reflected signals (echo signals) from the object for imaging the object, an arrayed ultrasonic probe 10 performing the function of transmitting/receiving ultrasonic signals is used as shown in FIG. 3. The ultrasonic probe 10 is connected to an ultrasonic probe control unit 15 via a cable 11. Also, a screen 16 is installed in the ultrasonic diagnostic apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An ultrasonic probe, comprising:
    a piezoelectric element;
    a first acoustic matching layer provided on the front face of the piezoelectric element and formed of a solid inorganic material; and
    a second acoustic matching layer provided on the first acoustic matching layer and formed of a mixture of an organic resin and 10 to 30% by volume of oxide powder with a density of 6.5 g/cm³ or more.
2. The ultrasonic probe according to claim 1, wherein the oxide powder is of a perovskite structure comprising 50% or more of PbO and 1% or more of $Nb_2O_5$.
3. The ultrasonic probe according to claim 1, wherein the oxide powder is selected from the group consisting of $CeO_2$, $Pr_2O_3$, $Nd_2O_3$, $Yb_2O_3$, and $Lu_2O_3$.
4. The ultrasonic probe according to claim 1, wherein the first acoustic matching layer is formed of a solid inorganic material selected from the group consisting of a ceramics including $SiO_2$, MgO and $Al_2O_3$, a ceramics including $Si_3N_4$, AlN, $Al_2O_3$ and $ZrO_2$, a ceramics including calcium silicate and lithium aluminosilicate, a fluorophlogopite ceramics, and a hexagonal boron nitride ceramics.
5. The ultrasonic probe according to claim 1, wherein the piezoelectric element includes a piezoelectric material and a pair of electrodes formed on the front face and the back face of the piezoelectric material.
6. The ultrasonic probe according to claim 5, wherein the piezoelectric material is formed of a single crystalline material having a composition represented by:

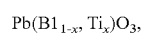

where $0.3 \leq x \leq 0.6$, and B1 is at least one element selected from the group consisting of Zr, Sn and Hf.

7. The ultrasonic probe according to claim 5, wherein the piezoelectric material is formed of a single crystalline material represented by:

$$Pb(B1, B2)_{1-x}Ti_xO_3,$$

where $0.04 \leq x \leq 0.55$, B1 is at least one element selected from the group consisting of Zn, Mg, Ni, Sc, In and Yb, and B2 is at least one element selected from the group consisting of Nb and Ta.

8. The ultrasonic probe according to claim 1, further comprising an acoustic lens formed on the second acoustic matching layer.

9. The ultrasonic probe according to claim 1, further comprising a third acoustic matching layer formed on the second acoustic matching layer.

10. The ultrasonic probe according to claim 9, further comprising an acoustic lens formed on the third acoustic matching layer.

11. The ultrasonic probe according to claim 1, further comprising a backing material provided on the back face of the piezoelectric element.

12. The ultrasonic probe according to claim 1, wherein the piezoelectric element, the first acoustic matching layer, and the second acoustic matching layer are one-dimensionally or two-dimensionally arrayed.

13. An ultrasonic diagnostic apparatus, comprising:
an ultrasonic probe comprising: an acoustic backing layer; a piezoelectric element provided on the front face of the acoustic backing layer; a first acoustic matching layer provided on the front face of the piezoelectric element and formed of a solid inorganic material; a second acoustic matching layer provided on the front face of the first acoustic matching layer and formed of a mixture of an organic resin and 10 to 30% by volume of oxide powder with a density of 6.5 g/cm³ or more; and an acoustic lens provided on the front face of the second acoustic matching layer, and
a ultrasonic-probe control unit connected to the ultrasonic probe via a cable.

14. The apparatus according to claim 13, wherein the oxide powder is of a perovskite structure comprising 50% or more of PbO and 1% or more of $Nb_2O_5$.

15. The apparatus according to claim 13, wherein the oxide powder selected from the group consisting of $CeO_2$, $Pr_2O_3$, $Nd_2O_3$, $Yb_2O_3$, and $Lu_2O_3$.

16. The apparatus according to claim 13, wherein the first acoustic matching layer is formed of a solid inorganic material selected from the group consisting of a ceramics including $SiO_2$, MgO and $Al_2O_3$, a ceramics including $Si_3N_4$, AlN, $Al_2O_3$ and $ZrO_2$, a ceramics including calcium silicate and lithium aluminosilicate, a fluorophlogopite ceramics, and a hexagonal boron nitride ceramics.

17. The apparatus according to claim 13, wherein the piezoelectric element includes a piezoelectric material and a pair of electrodes formed on the front face and the back face of the piezoelectric material.

18. The apparatus according to claim 17, wherein the piezoelectric material is formed of a single crystalline material having a composition represented by:

$$Pb(B1_{1-x}, Ti_x)O_3,$$

where $0.3 \leq x \leq 0.6$, and B1 is at least one element selected from the group consisting of Zr, Sn and Hf.

19. The apparatus according to claim 17, wherein the piezoelectric material is formed of a single crystalline material represented by:

$$Pb(B1, B2)_{1-x}Ti_xO_3,$$

where $0.04 \leq x \leq 0.55$, B1 is at least one element selected from the group consisting of Zn, Mg, Ni, Sc, In and Yb, and B2 is at least one element selected from the group consisting of Nb and Ta.

20. The apparatus according to claim 13, wherein the piezoelectric element, the first acoustic matching layer, and the second acoustic matching layer are one-dimensionally or two-dimensionally arrayed.

* * * * *